United States Patent
Wang et al.

(10) Patent No.: US 10,729,397 B2
(45) Date of Patent: Aug. 4, 2020

(54) X-RAY PHASE CONTRAST AND DARK-FIELD INFORMATION EXTRACTION WITH ELECTRIC FRINGE SCANNING AND/OR ACTIVE PIXEL PROCESSING

(71) Applicants: Rensselaer Polytechnic Institute, Troy, NY (US); University of Central Florida, Orlando, FL (US)

(72) Inventors: Ge Wang, Loudonville, NY (US); Wenxiang Cong, Albany, NY (US); Zaifeng Shi, Tianjin (CN); Shuo Pang, Oviedo, FL (US)

(73) Assignees: Rensselaer Polutechnic Institute, Troy, NY (US); University of Central Florida, Orlando, FL (US)

( * ) Notice: Subject to any disclaimer, the term of this patent is extended or adjusted under 35 U.S.C. 154(b) by 217 days.

(21) Appl. No.: 15/741,026

(22) PCT Filed: Jul. 20, 2016

(86) PCT No.: PCT/US2016/043154
§ 371 (c)(1),
(2) Date: Dec. 29, 2017

(87) PCT Pub. No.: WO2017/015381
PCT Pub. Date: Jan. 26, 2017

(65) Prior Publication Data
US 2018/0192980 A1    Jul. 12, 2018

Related U.S. Application Data

(60) Provisional application No. 62/194,452, filed on Jul. 20, 2015.

(51) Int. Cl.
A61B 6/00 (2006.01)
A61B 6/03 (2006.01)

(52) U.S. Cl.
CPC ............ *A61B 6/484* (2013.01); *A61B 6/4035* (2013.01); *A61B 6/4291* (2013.01); *A61B 6/032* (2013.01)

(58) Field of Classification Search
CPC ..... A61B 6/484; A61B 6/4035; A61B 6/4291; A61B 6/032
See application file for complete search history.

(56) References Cited

U.S. PATENT DOCUMENTS 7,453,981 B2    11/2008  Baumann et al.
7,492,871 B2    2/2009   Popescu et al.
(Continued)

FOREIGN PATENT DOCUMENTS

EP      0161324 A1     11/1985
WO      2014154188 A1  10/2014
(Continued)

OTHER PUBLICATIONS

International Search Report/Written Opinion, PCT International Application No. PCT/US2016/043154, PCT/ISA/220, PCT/ISA/210, PCT/ISA/237, dated Nov. 1, 2016.

*Primary Examiner* — Christine S. Kim
(74) *Attorney, Agent, or Firm* — Murtha Cullina LLP; Anthony P. Gangemi

(57) ABSTRACT

Novel and advantageous systems and methods for performing X-ray imaging by extracting X-ray phase-shift and/or dark-field information through a detector that has built-in G2 functionality are provided. Grating translation can be replaced by an electrical operation in the detection procedure, thereby eliminating the need for the analyzer grating and the typical mechanical stepping process.

20 Claims, 3 Drawing Sheets

(56) References Cited

U.S. PATENT DOCUMENTS

| | | |
|---|---|---|
| 9,066,649 B2 | 6/2015 | Roessl et al. |
| 9,600,910 B2 | 3/2017 | Wang et al. |
| 9,730,657 B2 | 8/2017 | Wang et al. |
| 2015/0131783 A1* | 5/2015 | Sato ................ G01T 1/2928 378/82 |
| 2015/0157286 A1 | 6/2015 | Wang et al. |
| 2016/0041276 A1* | 2/2016 | Kawanabe ............ G01T 1/247 378/62 |
| 2016/0113602 A1 | 4/2016 | Wang et al. |
| 2016/0135769 A1 | 5/2016 | Wang et al. |
| 2016/0166852 A1 | 6/2016 | Wang et al. |
| 2017/0043041 A1 | 2/2017 | Wang et al. |
| 2017/0360385 A1 | 12/2017 | Wang et al. |
| 2017/0362585 A1 | 12/2017 | Wang et al. |

FOREIGN PATENT DOCUMENTS

| | | |
|---|---|---|
| WO | 2015164405 A1 | 10/2015 |
| WO | 2016106348 A1 | 6/2016 |
| WO | 2016118960 A1 | 7/2016 |
| WO | 2016154136 A1 | 9/2016 |
| WO | 2016197127 A1 | 12/2016 |
| WO | 2017015381 A1 | 1/2017 |
| WO | 2017019782 A1 | 2/2017 |
| WO | 2017048856 A1 | 3/2017 |
| WO | 2017083849 A1 | 5/2017 |
| WO | 2017143247 A1 | 8/2017 |
| WO | 2017176976 A1 | 10/2017 |
| WO | 2017205379 A2 | 11/2017 |

\* cited by examiner

X-RAY PHASE CONTRAST AND DARK-FIELD INFORMATION EXTRACTION WITH ELECTRIC FRINGE SCANNING AND/OR ACTIVE PIXEL PROCESSING

CROSS-REFERENCE TO RELATED APPLICATIONS

This application is a national stage application of International Patent Application No. PCT/US2016/043154, filed Jul. 20, 2016 which claims the benefit of U.S. Provisional Application Ser. No. 62/194,452, filed Jul. 20, 2015, both of which are incorporated herein by reference in their entireties, including any figures, tables, and drawings.

BACKGROUND OF THE INVENTION

X-ray imaging is a powerful tool in many fundamental and practical applications. As a primary example, X-ray computed tomography (CT) is a cornerstone of modern hospitals and clinics. The dominating theory of X-ray imaging is generally based on the attenuation contrast mechanism.

X-ray gratings have been used for hybrid CT imaging in terms of attenuation, refraction, and small-angle scattering. This grating-based approach represents a paradigm shift in X-ray CT from gray-scale (attenuation) to true-color (attenuation, refraction, and small-angle scattering, which is also referred to as dark-field, and spectral) imaging.

In conventional X-ray imaging, the image contrast arises from varying linear attenuation coefficients. Attenuation-contrast-based imaging exhibits good performance only when strong attenuators are embedded in a weakly absorbing matrix, such as in the cases of bone-tissue and tissue-air interfaces. However, biological soft tissues include mainly light elements (e.g., hydrogen, carbon, nitrogen, and oxygen), and their compositions are quite homogeneous with little density variation. The attenuation-contrast between soft tissue features is often insufficient to reflect pathological changes.

In particular, many healthy tissues display similar characteristics in current X-ray images as those of diseased tissues, such as tumors. For example, fibro-glandular tissue can have a density of 1.035 $cm^{-3}$ and an attenuation coefficient of 0.80 $cm^{-1}$, and cancerous tissue can have a density of 1.045 $cm^{-3}$ and an attenuation coefficient of 0.85 $cm^{-1}$. Given inherent measurement noise, it is challenging to discern such cancerous tissue from the healthy tissue, as well as other soft tissue features such as those reflecting musculoskeletal healing. Therefore, attenuation-contrast-based imaging is unable to differentiate early-stage tumors and soft tissues.

X-ray small-angle scattering, or dark-field, imaging acquires photons slightly deflected from the primary beam through an object. Small-angle scattering signals reflect structural texture on length scales between 1 nanometer (nm) to several hundred nm. This imaging mode can reveal subtle texture of tissues. For example, the growth of tumors causes remarkable differences in small-angle scattering patterns from that of healthy tissues. It is clinically important that the structural variation in a tumor modifies the refractive index. The propagation of X-rays in a medium is characterized by the complex index of refraction. The cross section of an X-ray phase shift is one thousand times larger than that of the linear attenuation in the 20 keV-100 keV range. This implies that phase-contrast imaging has much higher sensitivity for light elements than does attenuation-contrast imaging.

The contrast-to-noise ratio of differential phase contrast CT images is superior to that of its attenuation-contrast CT counterpart. Therefore, phase-contrast imaging can observe unique critical structures of soft biological tissues. Moreover, the refractive index of tissues is inversely proportional to the square of the X-ray energy while the absorption coefficient decreases as the fourth power of the X-ray energy. Hence, X-ray phase-contrast imaging is suitable to operate at higher energies (e.g., >30 keV) for lower radiation dose than is attenuation imaging. Higher energy X-ray imaging can be useful for imaging and studies on large animals and/or human patients.

In X-ray grating-based imaging, X-ray phase-shift and dark-field information is currently extracted using the fringe scanning method through shifting of the analyzer grating. However, major challenges include the difficulty in making an analyzer grating (often known as G2), the requirement of a high-precision mechanical device, and the long data acquisition time due to the use of the phase stepping procedure.

BRIEF SUMMARY

Embodiments of the subject invention provide novel and advantageous systems and methods for performing X-ray imaging by extracting X-ray phase-shift and/or dark-field information through a detector that has built-in G2 functionality, as well as manipulation thereof. Grating translation can be replaced by an electrical operation in the detection procedure. That is, the typical mechanical stepping process can be omitted and replaced by an electrical steering process and/or mechanism, and the analyzer grating (G2) can be omitted by having its functionality combined with (or incorporated into) the detector itself. The systems and methods of embodiments of the subject invention present new opportunities in phase-contrast X-ray imaging (or X-ray grating-based imaging), shorten X-ray grating-based imaging time, increase dose utilization, and have many applications, including biomedical applications.

In an embodiment, an imaging system can comprise an X-ray radiation source and a detector for detecting X-ray radiation from the radiation source, wherein the detector comprises a semiconductor material and at least one electrode attached to the semiconductor material for providing an electric field. The system can further comprise a phase grating positioned between the radiation source and the detector, and a source grating positioned between the radiation source and the phase grating, and the system can specifically exclude an analyzer grating.

In another embodiment, a system as described herein can be used to perform a method of imaging, the method comprising: providing X-ray radiation to a sample to be imaged using the X-ray radiation source; collecting the X-ray radiation with the detector; and analyzing data from the detector to obtain an image. The electric field can be modulated by increasing or decreasing the voltage of the electric field from a zero voltage to a positive or negative voltage. Differently-shifted moiré-fringe patterns can be detected at a plurality of time intervals while the electric field is modulated, thereby resulting in a recorded intensity measure as a function of voltage. X-ray diffraction fringes, phase-shift information, and dark-field information can be extracted from the data from the detector.

DETAILED DESCRIPTION

Embodiments of the subject invention provide novel and advantageous systems and methods for performing X-ray imaging by extracting X-ray phase-shift and/or dark-field information through a detector that has built-in G2 functionality, as well as manipulation thereof. Grating translation can be replaced by an electrical operation in the detection procedure. That is, the typical mechanical stepping process can be omitted and replaced by an electrical steering process and/or mechanism, and the analyzer grating (G2) can be omitted by having its functionality combined with (or incorporated into) the detector itself. The systems and methods of embodiments of the subject invention present new opportunities in phase-contrast X-ray imaging (or X-ray grating-based imaging), shorten X-ray grating-based imaging time, increase dose utilization, and have many applications, including biomedical applications. In some embodiments, the detector can be located at a Talbot distance, or fractional Talbot distance, from the phase grating, where the interference fringes are formed.

Figure 1:
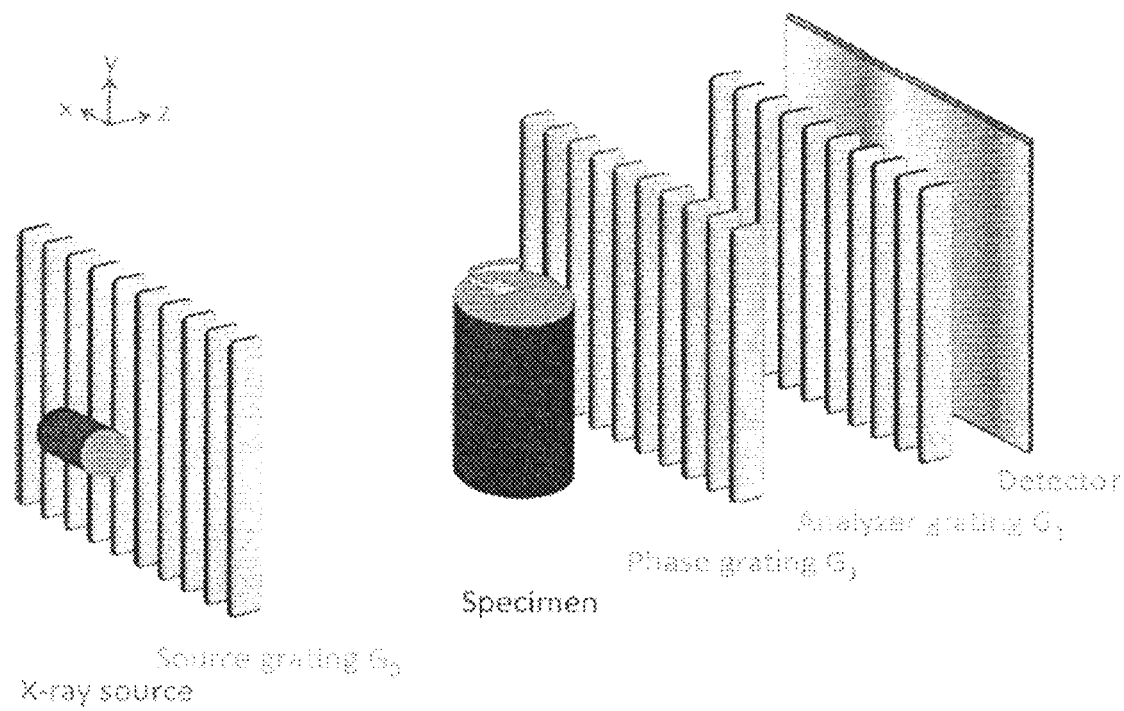
FIG. 1 shows a grating-based X-ray interferometer that can be used in X-ray grating-based imaging.

FIG. 1 shows a grating-based X-ray interferometer that can be used in X-ray grating-based imaging (phase-contrast X-ray imaging). FIG. 1 is from Burger et al. (Opt. Express 22, 32107-32118 2014; which is hereby incorporated herein by reference in its entirety). Referring to FIG. 1, the interferometer can include a phase grating G1 and an analyzer grating G2. The system can also include an X-ray source, a source grating G0, and a detector. The specimen being imaged can be placed between the source grating G0 and the phase grating G1. Phase-shift and dark-field information can be extracted using phase stepping, where the analyzer grating G2 or phase grating G1 is scanned over one G2 grating period.

According to embodiments of the subject invention, the analyzer grating G2 can be omitted by having its functionality combined with (or incorporated into) the detector itself. All the gratings can therefore be kept stationary, thereby decreasing scanning time and inhibiting the chances for mechanical error. The moiré-fringe pattern can be shifted by varying an additional electric field across the detector (e.g., across a semiconductor material in a direct X-ray detector).

Figure 2:
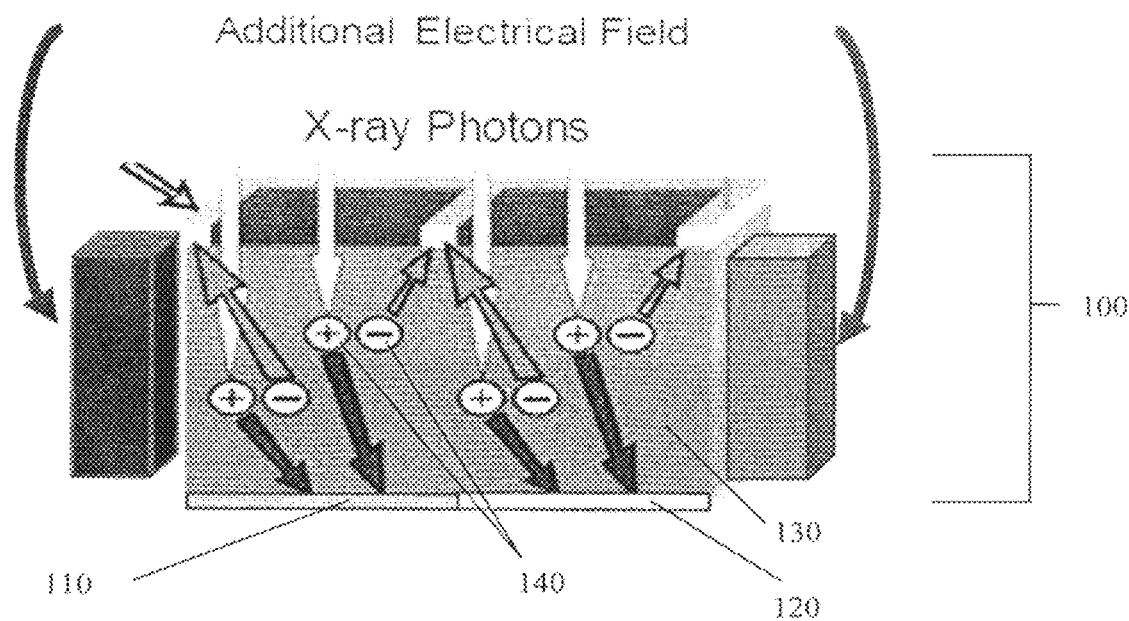
FIG. 2 shows a cross-sectional view of a detector according to an embodiment of the subject invention.

FIG. 2 shows a cross-sectional view of a detector according to an embodiment of the subject invention. Referring to FIG. 2, a detector pixel 100 of the detector 100 can have at least one electrode 110,120 connected to the bulk material 130 (e.g., semiconductor material) of the detector. When X-rays irradiate the semiconductor material 130 in the detector, photo-electrons are generated, producing electron-hole pairs 140 in the semiconductor material 130. The electrode(s) 110,120 connected to the semiconductor material 130 can acquire a current signal. Though FIG. 2 depicts two electrodes 110,120 connected to the bulk material 130 of the detector pixel 100, embodiments are not limited thereto. Each detector pixel can include a single electrode or a plurality of electrodes; such a plurality of electrodes can include two electrodes, three electrodes, four electrodes, or more. In a certain embodiment, the detector can have one electrode or the plurality of electrodes attached to the entire detector (instead of to each detector pixel).

In many embodiments, each electrode present in the detector can be a micro-electrode. The size of each micro-electrode can be, for example, half of the analyzer grating G2 period (i.e., the period of the analyzer grating G2 that would otherwise be present if its functionality was not combined with the detector).

The additional electric field can steer electron-hole pairs horizontally in the semiconductor material 130. Homogeneity of the electric field can be advantageous for the moiré-fringe pattern to be shifted consistently; otherwise, further processing may be needed to extract required information. In an embodiment, to improve the homogeneity of the additional electric field, the electric field can be added across only a small number (e.g., 45% or less, 40% or less, 30% or less, 20% or less, 15% or less, 10% or less, or 5% or less) of electrodes attached to the semiconductor material 130 of the detector.

In the data acquisition process, the additional electric field can be modulated by increasing (or decreasing) the voltage of the electric field from a zero voltage to a positive or negative voltage so that differently-shifted moiré-fringe patterns can be detected at various time intervals. The voltage setting can be optimized for a high signal-to-noise ratio. The recorded intensity measure as a function of voltage can be periodic with the same period of G2 (i.e., the period of the analyzer grating G2 that would otherwise be present if its functionality was not combined with the detector). From these data, the X-ray diffraction fringes, and the phase-shift and dark-field information, can be extracted in the same way as with the traditional stepping method.

Specifically, the intensity of the interference pattern in each detector pixel can be written as a Fourier series with negligible contributions of harmonics higher than the first order:

$$I(m,n,x_v) \approx a_0(m,n) + a_1(m,n)\cos(kx_v + \varphi(m,n)). \quad (1)$$

Using Equation (1), the recorded image I(m, n, $x_v$) at a given view angle can be used to extract transmission, differential phase shift, and dark-field signals, respectively. This can also be done using a photon-counting detector so that spectral information is included. The phase angle φ(m, n) is directly related to the local gradient of the phase shift $$\frac{\partial \Phi(m, n)}{\partial x},$$

where Φ(m, n) represents the phase shift of the wave front.

Though two electrodes are depicted in FIG. 2, single or multiple electrodes can be used, and their dimensions can be uniform or non-uniform (or some can be uniform while others are non-uniform). Also, in an embodiment, spacing between electrodes can be used, over which some electron-hole pairs may disappear at the cost of dose efficiency.

If electrodes are sufficiently small, no shifting will be needed, because the fringe pattern can be directly recorded.

Such small electrodes and associated circuitry can be expensive in certain cases. In many embodiments of the subject invention, cost-effectiveness of the system or method can be optimized, which may not necessarily include using electrodes small enough such that no shifting is needed. Furthermore, the signals directly recorded by the electrodes can be processed for more information as described herein.

In some embodiments, the detector can include active pixel sensors. Active pixel sensors, in which each electrode has its own amplifier(s) and charge-to-voltage converter(s), are applicable in active X-ray phase-contrast imaging applications. Because the photo-electrons from each pixel can be extracted with multiple electrodes independently, the resulting signals can be processed to detect the sub-pixel shift of the X-ray fringes. Here, one pixel can be treated as the smallest unit of the sensor array, and the electrode patterns can be identical for each pixel as an example, though embodiments are not limited thereto (electrode patterns need not be identical for each pixel).

Figures 3A, 3B:
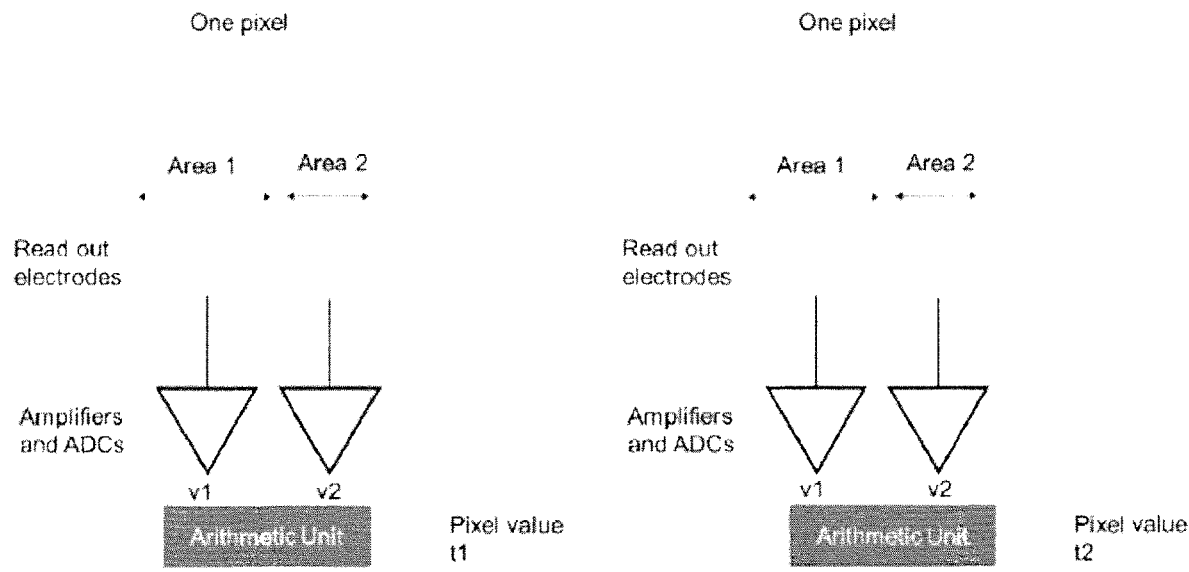
FIG. 3A shows an active pixel with according to embodiment of the subject invention.
FIG. 3B shows an active pixel with an identical electrode pattern to that of the active pixel in FIG. 3A.

FIGS. 3A and 3B show two active pixels with identical electrode patterns. Referring to FIGS. 3A and 3B, each pixel includes two electrodes. Though an asymmetric configuration for the electrodes is depicted in FIGS. 3A and 3B, the electrodes can be symmetric or asymmetric to capture a sub-pixel intensity change. Each electrode can have its own amplifier and analog-to-digital converter (ADC). The signals from the electrodes after the analog-to-digital conversion can then be processed by an on-chip arithmetic unit to output a pixel value. The arithmetic unit can perform simple calculations, such as addition, subtraction, and multiplication, and it can also serve as a register, which performs a simple arithmetic operation on delayed input values. In various embodiments, each electrode can have its own arithmetic unit, each pixel can have a single arithmetic unit shared by all electrodes thereon, the chip can include a plurality of arithmetic units such that some pixels share the same arithmetic unit, or the chip can have a single arithmetic unit shared by all pixels and all electrodes.

Figure 4:
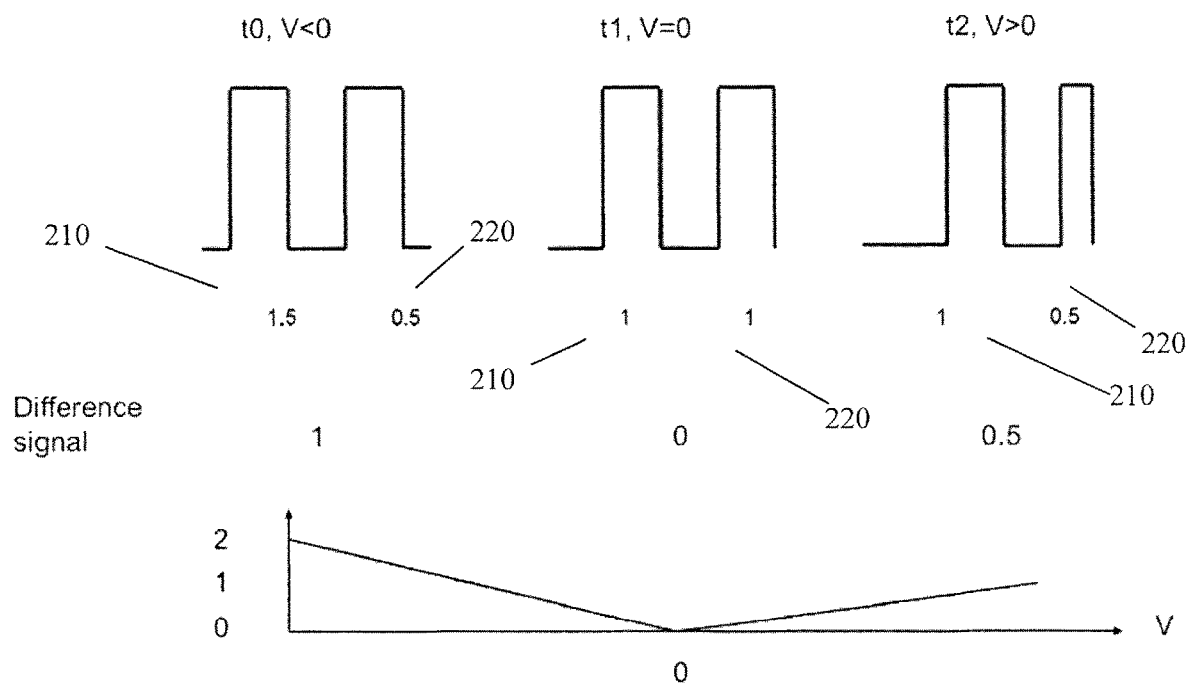
FIG. 4 shows differential operation of a two-electrode readout pixel according to embodiment of the subject invention.

FIG. 4 shows an example of a differential operation of a two-electrode 210,220 readout pixel, allowing detection of a sub-pixel phase-shift amplitude and direction. FIG. 4 demonstrates that both the sub-pixel phase stepping of the irradiance profile and the direction of the phase stepping (with an asymmetric electrode-pair) can be detected with a difference operation; i.e., the output signal is the difference between the signals from two electrodes 210,220, as shown in FIG. 4. Referring to FIG. 4 and assuming that there are two fringe periods on each pixel, the first electrode 210 has three quarters of the total pixel area while the second electrode 220 has one quarter of the pixel area. These proportions are for exemplary purposes only and should not be construed as limiting. At time t0, the applied voltage of the additional electric field V is less than 0, and the total signal in the area of the first electrode 210 is 1.5, while that of the second electrode 220 is 0.5. The intensity profile is shown on the left, above the electrodes 210,220. The readout signal after the arithmetic unit is 1. At time t1, the applied voltage is 0, and the readout signal is 0 as shown in the middle of the "difference signal" row of FIG. 4. At time t2, the applied voltage is greater than zero, and the charge at the second electrode 220 can only be partially converted to the readout, resulting in an asymmetric readout function, as shown in the plot at the bottom portion of FIG. 4. During the data acquisition process, the shift voltage can drive a scan over one period of the X-ray diffraction fringe, and the phase contrast information can be easily computed.

Figure 5:
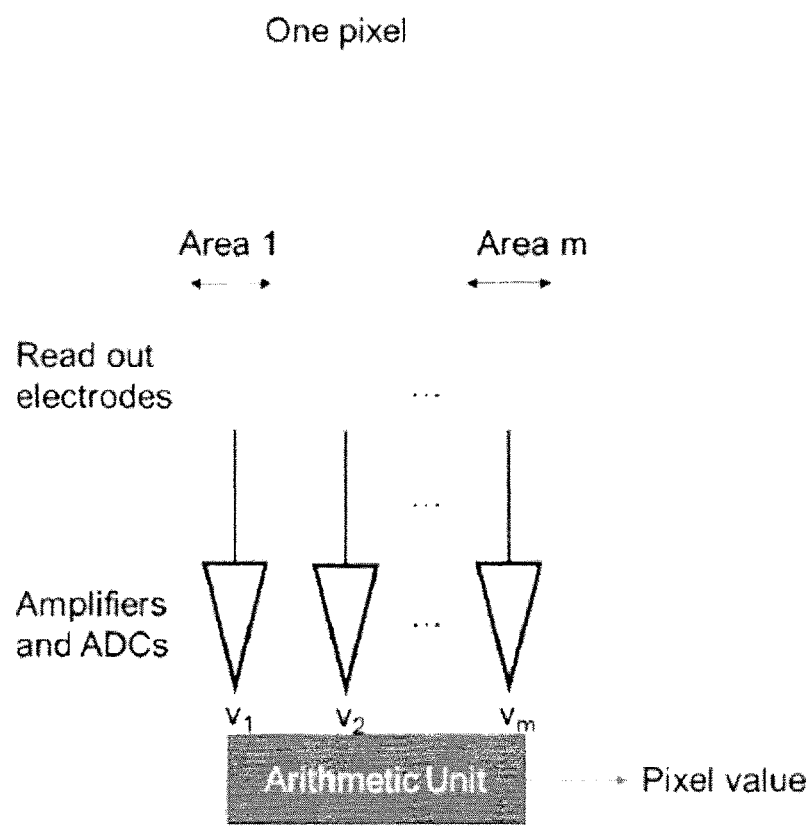
FIG. 5 shows a pixel having multiple electrodes according to an embodiment of the subject invention.

FIG. 5 shows a pixel having multiple electrodes (m electrodes, where m is an integer) according to an embodiment of the subject invention. Though FIG. 5 depicts the electrodes having uniform area, embodiments are not limited thereto. Finer sub-pixel shift can be detected by using multiple electrodes, as in FIG. 5. If the periodicity of the X-ray fringes and the pixel electrodes matches, a simple difference between signals from two adjacent electrodes can be used to calculate both differential phase-shift and dark-field information.

Figures 6A, 6B:
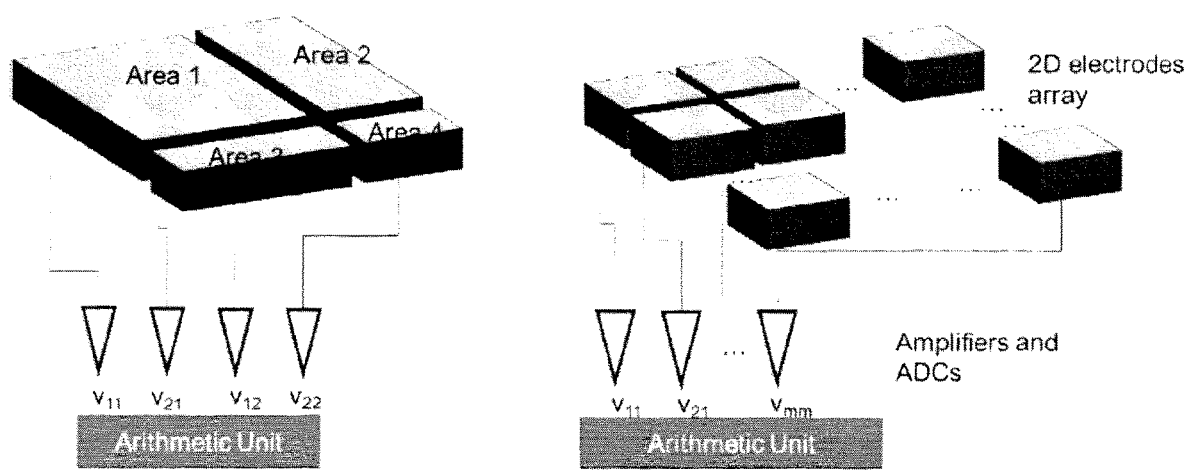
FIG. 6A shows configurations of a two-dimensional electrode array that can be implemented in a pixel of a detector according to an embodiment of the subject invention.
FIG. 6B shows configurations of a two-dimensional electrode array that can be implemented in a pixel of a detector according to an embodiment of the subject invention.

FIGS. 6A and 6B show configurations of two-dimensional electrode arrays that can be implemented in pixels of a detector according to embodiments of the subject invention. Referring to FIG. 6A, the electrodes of the array can have different areas as depicted, though embodiments are not limited thereto. Also, though FIG. 6A depicts four electrodes in the array, this is for exemplary purposes only. Referring to FIG. 6B, the areas of the electrodes can be uniform. Also, any reasonable number of electrodes can be present in the array. These two-dimensional configurations can be implemented to measure diffraction fringes on a plane.

According to embodiments of the subject invention, X-ray phase-shift and dark-field information can be extracted through a specially-designed detector that has built-in analyzer grating G2 functionality and manipulation. Grating translation can be replaced by an electrical operation in the detection procedure. The mechanical stepping process of the conventional art can be replaced by the electric steering mechanism, and the actual analyzer grating G2 can be omitted by having its functionality incorporated into the detector of the imaging system. The detector can be located at a Talbot distance, or a fractional Talbot distance, from the phase grating, where the interference fringes are formed, though embodiments are not limited thereto.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

An imaging system, comprising:
a radiation source (e.g., an X-ray source); and
a detector for detecting radiation (e.g., X-rays) from the radiation source, wherein the detector comprises a semiconductor material and at least one electrode attached to the semiconductor material for providing an electric field.

Embodiment 2

The system according to embodiment 1, further comprising a phase grating positioned between the radiation source and the detector.

Embodiment 3

The system according to embodiment 2, further comprising a source grating positioned between the radiation source and the phase grating.

Embodiment 4

The system according to embodiment 3, configured such that the subject to be imaged is positioned between the source grating and the phase grating.

Embodiment 5

The system according to embodiment 1, further comprising a source grating positioned between the radiation source and the detector.

Embodiment 6

The system according to any of embodiments 1-5, wherein the system excludes an analyzer grating.

Embodiment 7

The system according to any of embodiments 1-6, wherein the detector comprises a plurality of detector pixels, each comprising the semiconductor material of the detector, and wherein each detector pixel comprises at least one electrode attached to the semiconductor material.

Embodiment 8

The system according to embodiment 7, wherein each detector pixel comprises a plurality of electrodes attached to the semiconductor material.

Embodiment 9

The system according to embodiment 7, wherein each detector pixel comprises exactly two electrodes attached to the semiconductor material.

Embodiment 10

The system according to any of embodiments 1-9, wherein the detector further comprises an arithmetic unit connected to the at least one electrode.

Embodiment 11

The system according to any of embodiments 1-10, wherein the detector further comprises an amplifier connected to the at least one electrode.

Embodiment 12

The system according to any of embodiments 1-11, wherein the detector further comprises an analog-to-digital convertor (ADC) connected to the at least one electrode.

Embodiment 13

The system according to embodiment 9, wherein the detector further comprises an amplifier connected to the at least one electrode between the arithmetic unit and the at least one electrode.

Embodiment 14

The system according to any of embodiments 9 and 13, wherein the detector further comprises an ADC connected to the at least one electrode between the arithmetic unit and the at least one electrode.

Embodiment 15

The system according to any of embodiments 1-10, wherein the detector comprises a plurality of electrodes attached to the semiconductor material, and wherein the detector further comprises a plurality of amplifiers respectively connected to the plurality of electrodes.

Embodiment 16

The system according to any of embodiments 1-10 and 15, wherein the detector comprises a plurality of electrodes attached to the semiconductor material, and wherein the detector further comprises a plurality of ADCs respectively connected to the plurality of electrodes.

Embodiment 17

The system according to embodiment 9, wherein the detector comprises a plurality of electrodes attached to the semiconductor material, and wherein the detector further comprises a plurality of amplifiers respectively connected to the plurality of electrodes between the arithmetic unit and the respective electrode.

Embodiment 18

The system according to any of embodiments 9, wherein the detector comprises a plurality of electrodes attached to the semiconductor material, and wherein the detector further comprises a plurality of ADCs respectively connected to the plurality of electrodes between the arithmetic unit and the respective electrode.

Embodiment 19

The system according to any of embodiments 7-9, wherein each detector pixel further comprises an arithmetic unit connected to the at least one electrode.

Embodiment 20

The system according to any of embodiments 7-9 and 19, wherein each detector pixel further comprises an amplifier connected to the at least one electrode.

Embodiment 21

The system according to any of embodiments 7-9, 19, and 20, wherein each detector pixel further comprises an ADC connected to the at least one electrode.

Embodiment 22

The system according to embodiment 19, wherein each detector pixel further comprises an amplifier connected to the at least one electrode between the arithmetic unit and the at least one electrode.

Embodiment 23

The system according to any of embodiments 19 and 22, wherein each detector pixel further comprises an ADC connected to the at least one electrode between the arithmetic unit and the at least one electrode.

Embodiment 24

The system according to any of embodiments 7-9 and 19, wherein each detector pixel comprises a plurality of electrodes attached to the semiconductor material, and wherein each detector pixel further comprises a plurality of amplifiers respectively connected to the plurality of electrodes.

Embodiment 25

The system according to any of embodiments 7-9, 19, and 24, wherein each detector pixel comprises a plurality of electrodes attached to the semiconductor material, and wherein each detector pixel further comprises a plurality of ADCs respectively connected to the plurality of electrodes.

Embodiment 26

The system according to embodiment 19, wherein each detector pixel comprises a plurality of electrodes attached to the semiconductor material, and wherein each detector pixel further comprises a plurality of amplifiers respectively connected to the plurality of electrodes between the arithmetic unit and the respective electrode.

Embodiment 27

The system according to embodiment 19, wherein each detector pixel comprises a plurality of electrodes attached to the semiconductor material, and wherein each detector pixel further comprises a plurality of ADCs respectively connected to the plurality of electrodes between the arithmetic unit and the respective electrode.

Embodiment 28

The system according to any of embodiments 7-9, wherein each detector pixel comprises a plurality of electrodes attached to the semiconductor material, and wherein each detector pixel further comprises a plurality of arithmetic units respectively connected to the plurality of electrodes.

Embodiment 29

The system according to embodiment 28, wherein each detector pixel further comprises a plurality of amplifiers respectively connected to the plurality of electrodes between the respective arithmetic unit and the respective electrode.

Embodiment 30

The system according to any of embodiments 28-29, wherein each detector pixel further comprises a plurality of ADCs respectively connected to the plurality of electrodes between the respective arithmetic unit and the respective electrode.

Embodiment 31

The system according to any of embodiments 7-30, wherein each detector pixel comprises a plurality of electrodes attached to the semiconductor material and arranged in an array within said detector pixel.

Embodiment 32

The system according to any of embodiments 7-31, wherein each detector pixel comprises a plurality of electrodes attached to the semiconductor material, and wherein an area of each electrode within a given detector pixel is the same as that of all other electrodes within said detector pixel.

Embodiment 33

The system according to any of embodiments 1-32, wherein the detector comprises a plurality of electrodes attached to the semiconductor material, and wherein an area of each electrode is the same as that of all other electrodes.

Embodiment 34

The system according to any of embodiments 7-31, wherein each detector pixel comprises a plurality of electrodes attached to the semiconductor material, and wherein an area of each electrode within a given detector pixel is different from that of at least one other electrode within said detector pixel.

Embodiment 35

The system according to any of embodiments 7-31 and 34, wherein each detector pixel comprises a plurality of electrodes attached to the semiconductor material, and wherein an area of each electrode within a given detector pixel is different from that of all other electrodes within said detector pixel.

Embodiment 36

The system according to any of embodiments 1-31, 34, and 35, wherein the detector comprises a plurality of electrodes attached to the semiconductor material, and wherein an area of each electrode is the different from that of at least one other electrode.

Embodiment 37

The system according to any of embodiments 1-31 and 34-36, wherein the detector comprises a plurality of electrodes attached to the semiconductor material, and wherein an area of each electrode is the different from that of all other electrodes.

Embodiment 38

The system according to any of embodiments 1-37, wherein the electrode(s) present in the detector provide an electric field that steers electron-hole pairs horizontally (parallel to a detection surface of the detector that faces the radiation source) in the semiconductor material of the detector.

Embodiment 39

The system according to any of embodiments 1-38, wherein the electrode(s) present in the detector provide a homogenous electric field in the semiconductor material of the detector.

Embodiment 40

The system according to any of embodiments 1-39, wherein the detector comprises a plurality of electrodes, and wherein the electric field is added across 45% or less of the electrodes of the detector.

Embodiment 41

The system according to any of embodiments 1-39, wherein the detector comprises a plurality of electrodes, and wherein the electric field is added across 40% or less of the electrodes of the detector.

Embodiment 42

The system according to any of embodiments 1-39, wherein the detector comprises a plurality of electrodes, and wherein the electric field is added across 30% or less of the electrodes of the detector.

Embodiment 43

The system according to any of embodiments 1-39, wherein the detector comprises a plurality of electrodes, and wherein the electric field is added across 20% or less of the electrodes of the detector.

Embodiment 44

The system according to any of embodiments 1-39, wherein the detector comprises a plurality of electrodes, and wherein the electric field is added across 15% or less of the electrodes of the detector.

Embodiment 45

The system according to any of embodiments 1-39, wherein the detector comprises a plurality of electrodes, and wherein the electric field is added across 10% or less of the electrodes of the detector.

Embodiment 46

The system according to any of embodiments 1-39, wherein the detector comprises a plurality of electrodes, and wherein the electric field is added across 5% or less of the electrodes of the detector.

Embodiment 47

The system according to any of embodiments 1-46, wherein each electrode present is a micro-electrode.

Embodiment 48

The system according to embodiment 47, wherein the size (e.g., length, width, or longest dimension in any direction) of each micro-electrode is half of the grating period of the (omitted) analyzer grating whose functionality is incorporated into the detector.

Embodiment 49

The system according to any of embodiments 1-48, wherein the system further comprises a phase grating positioned between the X-ray source and the detector, and wherein the detector is positioned a Talbot distance, or fractional Talbot distance, from the phase grating, where the interference fringes are formed.

Embodiment 50

A method of imaging using the system according to any of embodiments 1-49, the method comprising:
providing radiation (e.g., X-ray radiation) to a sample to be imaged using the radiation source;
collecting the radiation (e.g., X-ray radiation) with the detector; and analyzing data from the detector to obtain an image.

Embodiment 51

The method according to embodiment 52, further comprising modulating the electric field provided by the at least one electrode attached to the semiconductor material of the detector.

Embodiment 52

The method according to embodiment 51, wherein modulating the electric field comprises increasing (or decreasing) the voltage of the electric field from a zero voltage to a positive (or negative) voltage.

Embodiment 53

The method according to embodiment 52, further comprising detecting differently-shifted moiré-fringe patterns at a plurality of time intervals while the electric field is modulated, thereby resulting in a recorded intensity measure as a function of voltage.

Embodiment 54

The method according to embodiment 53, wherein the recorded intensity measure as a function of voltage is periodic with a period that is the same as the grating period of the (omitted) analyzer grating whose functionality is incorporated into the detector.

Embodiment 55

The method according to any of embodiments 50-54, wherein analyzing data from the detector to obtain an image comprises extracting diffraction fringes (e.g., X-ray diffraction fringes), phase-shift information, and dark-field information from the data from the detector.

Embodiment 56

The method according to any of embodiments 50-55, wherein the detector comprises a plurality of detector pixels, and wherein analyzing data from the detector to obtain an image comprises using the recorded image intensity measure $I(m, n, x_v)$ at a given view angle to extract transmission, differential phase shift, and dark-field signals, respectively, where $I(m, n, x_v)$ is represented by the following Fourier series:

$$I(m,n,x_v) \approx a_0(m,n) + a_1(m,n)\cos(kx_v + \varphi(m,n)).$$

Embodiment 57

The method according to embodiment 56, wherein the phase angle $\varphi(m, n)$ is directly related to the local gradient of the phase shift $$\frac{\partial \Phi(m, n)}{\partial x},$$

where $\Phi(m, n)$ represents the phase shift of the wave front.

Embodiment 58

The system according to any of embodiments 1-49, further comprising a (non-transitory) machine readable medium (e.g., computer readable medium) having machine-executable (e.g., computer executable) instructions (stored thereon) for performing the step of analyzing data from the detector according to the method of any of embodiments 50-57, wherein the machine readable medium is in operable communication with the detector.

Embodiment 59

The system according to any of embodiments 1-49 and 58, or the method according to any of embodiments 50-57, wherein the detector is a photon-counting detector, such that spectral information is included in data of the detector.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Shi et al., An edge-on charge-transfer design for energy-resolved x-ray detection, Physics in Medicine and Biology, Volume 61, Number 11, 2016

Wang et al., International Patent Application Publication No. WO2016/106348
Wang et al., U.S. Patent Application Publication No. 2015/0157286
Wang et al., U.S. Patent Application Publication No. 2015/0170361
Wang et al., U.S. Patent Application Publication No. 2015/0193927
Wang et al., International Patent Application Publication No. WO2015/164405
Wang et al., U.S. Patent Application Publication No. 2016/0113602
Wang et al., U.S. Patent Application Publication No. 2016/0135769
Wang et al., U.S. Patent Application Publication No. 2016/0166852
Wang et al., International Patent Application Publication No. WO2016/106348
Wang et al., International Patent Application No. PCT/US2016/014769
Wang et al., International Patent Application No. PCT/US2016/023460
Wang et al., International Patent Application No. PCT/US2016/036057
Burger et al., "Regularized iterative integration combined with non-linear diffusion filtering for phase-contrast x-ray computed tomography," Opt. Express 22, 32107-32118 (2014); http://www.opticsinfobase.org/oe/abstract.cfm?uri=oe-22-26-32107
U.S. Provisional Application Ser. No. 62/197,301

What is claimed is:

1. An imaging system, comprising:
   an X-ray radiation source; and
   a detector for detecting X-ray radiation from the radiation source, wherein the detector comprises a semiconductor material and at least one electrode attached to the semiconductor material for providing an electric field;
   wherein the at least one electrode of the detector provides an electric field that steers electron-hole pairs horizontally in the semiconductor material of the detector.

2. The system according to claim 1, further comprising a phase grating positioned between the radiation source and the detector, and a source grating positioned between the radiation source and the phase grating,
   wherein the system is configured such that a subject to be imaged is positioned between the source grating and the phase grating.

3. The system according to claim 1, wherein the detector comprises a plurality of detector pixels, each comprising the semiconductor material of the detector, and wherein each pixel comprises at least one electrode attached to the semiconductor material.

4. The system according to claim 3, wherein each detector pixel further comprises an arithmetic unit connected to the at least one electrode,
   wherein each detector pixel further comprises an amplifier connected to the at least one electrode, and
   wherein each detector pixel further comprises an ADC connected to the at least one electrode.

5. The system according to claim 1, wherein the detector further comprises an arithmetic unit connected to the at least one electrode,
   wherein the detector further comprises an amplifier connected to the at least one electrode, and
   wherein the detector further comprises an analog-to-digital converter (ADC) connected to the at least one electrode.

6. The system according to claim 1, wherein the detector comprises a plurality of electrodes attached to the semiconductor material, and wherein the detector further comprises a plurality of amplifiers respectively connected to the plurality of electrodes.

7. The system according to claim 1, wherein the at least one electrode of the detector provides a homogenous electric field in the semiconductor material of the detector.

8. The system according to claim 1, wherein the detector comprises a plurality of electrodes, and wherein the electric field is added across 45% or less of the electrodes of the detector.

9. The system according to claim 1, wherein each electrode present is a micro-electrode, and
wherein a length of each micro-electrode is half of a grating period of an analyzer grating whose functionality is incorporated into the detector.

10. The system according to claim 1, wherein the detector is a photon-counting detector, such that spectral information is included in data of the detector.

11. A method of imaging using the system according to claim 1, the method comprising:
providing X-ray radiation to a sample to be imaged using the X-ray radiation source;
collecting the X-ray radiation with the detector; and
analyzing data from the detector to obtain an image.

12. The method according to claim 11, further comprising modulating the electric field provided by the at least one electrode attached to the semiconductor material of the detector, and
wherein modulating the electric field comprises increasing or decreasing the voltage of the electric field from a zero voltage to a positive or negative voltage.

13. The method according to claim 12, further comprising detecting differently-shifted moiré-fringe patterns at a plurality of time intervals while the electric field is modulated, thereby resulting in a recorded intensity measure as a function of voltage, and
wherein the recorded intensity measure as a function of voltage is periodic with a period that is the same as a grating period of an analyzer grating whose functionality is incorporated into the detector.

14. The method according to claim 11, wherein analyzing data from the detector to obtain an image comprises extracting X-ray diffraction fringes, phase-shift information, and dark-field information from the data from the detector.

15. The method according to claim 11, wherein the detector comprises a plurality of detector pixels, and wherein analyzing data from the detector to obtain an image comprises using the recorded image intensity measure I(m, n,$x_v$) at a given view angle to extract transmission, differential phase shift, and dark-field signals, respectively, where I(m,n,$x_v$) is represented by the following Fourier series:

$$I(m,n,x_v) \approx a_0(m,n) + a_1(m,n)\cos(kx_v + \varphi(m,n)), \text{ and}$$

wherein a phase angle $\varphi$(m,n) is directly related to a local gradient of a phase shift $$\frac{\partial \Phi(m,n)}{\partial x},$$

where $\Phi$(m,n) represents the phase shift of a wave front.

16. The method according to claim 11, wherein the detector is a photon-counting detector, such that spectral information is included in data of the detector.

17. An imaging system, comprising:
an X-ray radiation source; and
a detector for detecting X-ray radiation from the radiation source, wherein the detector comprises a semiconductor material and a plurality of electrodes attached to the semiconductor material for providing an electric field;
wherein the electric field is added across 45% or less of the electrodes of the detector.

18. The system according to claim 17, wherein the detector further comprises an arithmetic unit connected to the at least one electrode,
wherein the detector further comprises an amplifier connected to the at least one electrode, and
wherein the detector further comprises an analog-to-digital converter (ADC) connected to the at least one electrode.

19. The system according to claim 17, wherein the detector comprises a plurality of detector pixels, each comprising the semiconductor material of the detector, and wherein each pixel comprises at least one electrode attached to the semiconductor material.

20. The system according to claim 19, wherein each detector pixel further comprises an arithmetic unit connected to the at least one electrode,
wherein each detector pixel further comprises an amplifier connected to the at least one electrode, and
wherein each detector pixel further comprises an ADC connected to the at least one electrode.

* * * * *